(12) United States Patent
Zhang et al.

(10) Patent No.: US 10,730,838 B2
(45) Date of Patent: Aug. 4, 2020

(54) GREEN PREPARATION METHOD FOR QUINOLINE COMPOUNDS

(71) Applicant: DALIAN UNIVERSITY OF TECHNOLOGY, Dalian (CN)

(72) Inventors: Sheng Zhang, Dalian (CN); Ming Bao, Dalian (CN); Waqar Ahmed, Dalian (CN); Xiaoqiang Yu, Dalian (CN); Xiujuan Feng, Dalian (CN)

(73) Assignee: DALIAN UNIVERSITY OF TECHNOLOGY, Dalian, Liaoning (CN)

( * ) Notice: Subject to any disclaimer, the term of this patent is extended or adjusted under 35 U.S.C. 154(b) by 0 days.

(21) Appl. No.: 16/346,510

(22) PCT Filed: Jun. 7, 2018

(86) PCT No.: PCT/CN2018/090255
§ 371 (c)(1),
(2) Date: Apr. 30, 2019

(87) PCT Pub. No.: WO2019/095678
PCT Pub. Date: May 23, 2019

(65) Prior Publication Data
US 2020/0079737 A1    Mar. 12, 2020

(30) Foreign Application Priority Data

Nov. 14, 2017    (CN) .......................... 2017 1 1119462

(51) Int. Cl.
| | | |
|---|---|---|
| *C07D 215/06* | (2006.01) | |
| *B01J 31/02* | (2006.01) | |
| *B01J 31/04* | (2006.01) | |
| *C07D 409/04* | (2006.01) | |

(52) U.S. Cl.
CPC ........ *C07D 215/06* (2013.01); *B01J 31/0225* (2013.01); *B01J 31/04* (2013.01); *C07D 409/04* (2013.01); *B01J 2231/324* (2013.01)

(58) Field of Classification Search
CPC .................................................. C07D 215/06
See application file for complete search history.

(56) References Cited

FOREIGN PATENT DOCUMENTS

| CN | 106366035 A | 2/2017 |
| CN | 106380446 A | 2/2017 |
| CN | 106674101 A | 5/2017 |
| CN | 107739333 A | 2/2018 |

OTHER PUBLICATIONS

Liu. European Journal of Organic Chemistry, 2012, 1583-1589 (Year: 2012).*
Ahmed, Waqar, et al. , "Bronsted Acid-Catalyzed Metal- and Solvent-Free Quinoline Synthesis from N-alkyl anilines and Alkynes or Alkenes," *Green Chemistry*, 2018 Issue 1, Nov. 28, 2017, pp. 261-265.
Huo, Dr. Congde, et al. "Auto-Oxidative Coupling of Glycine Derivatives," Angewandte Communications, Chemie, *A Journal of the German Chemical Society*, Willey Online Library, vol. 53, Issue 49, Dec. 1, 2014, Oct. 6, 2014, pp. 13544-13547.
Xu, Xuefeng et al., "HOTf-catalyzed Intermolecular Hydroamination Reactions of Alkenes and Alkynes with Anilines," *The Royal Society of Chemistry*, Advances, Issue 51, Apr. 28, 2015, pp. 40950-40952.

* cited by examiner

*Primary Examiner* — Noble E Jarrell
(74) *Attorney, Agent, or Firm* — Muncy, Geissler, Olds & Lowe, PC

(57) ABSTRACT

Pharmaceutical and chemical intermediates and related chemistry providing a green preparation method for quinoline compounds. N-Substituted arylamine derivatives as raw material react with arylacetylene or arylethylene derivatives for 24 hours at 80° C.-160° C. in the presence of Brønsted acid catalyst and oxidant without solvent, to obtain quinoline compounds. Beneficial characteristics include convenient operation, mild reaction conditions, environmentally friendly property and possibility of realizing industrialization, and provides the quinoline compounds in high yields. The quinoline compounds synthesized by this method can be further functionalized into various compounds which have potential applications in development and research of natural products, functional materials and fine chemicals.

3 Claims, 16 Drawing Sheets

GREEN PREPARATION METHOD FOR QUINOLINE COMPOUNDS

TECHNICAL FIELD

The current invention belongs to the technical fields of pharmaceutical and chemical intermediates and related chemistry, which provides a green preparation method for quinoline compounds.

BACKGROUND

A quinoline compound is very important structural unit in organic chemistry and has important application value in the fields of medicines, pesticides, dyes, functional materials and spices. Since the quinoline has been separated from coal tar by Runge in 1834, how to synthesize quinoline derivatives chemically has been a hotspot for organic synthetic chemists.

Classical chemical methods of organic synthesis of the quinoline derivatives include Skraup-Doebner-von Miller synthesis, Combes-Conrad-Limpach synthesis, Friedländer synthesis and Pfitzinger synthesis [Fallah-Mehrjardi M., Mini-Rev. Org. Chem., 2017, 14, 187]. These synthetic methods have a critical disadvantage that reaction is usually conducted in high temperature and strong acid systems, which lead to high requirements for equipment and serious environmental pollution in industrial production. In recent years, a transition metal-catalyzed coupling reaction has been gradually concerned for its high efficiency, and has become an important method for synthesis of the quinoline compound [Prajapati S. M., Patel K. D., Vekariya R. H., Panchal S. N., Patel H. D., RSC Adv., 2014, 4, 24463]. Although the transition metal-catalyzed method avoids the use of inorganic acid such as concentrated sulfuric acid or concentrated hydrochloric acid, a transition metal catalyst still has the defect of the difficulty in separation and recovery of the catalyst in the process of catalytic synthesis of the quinoline derivatives. Therefore, it is of great significance to develop a green synthetic method of quinoline compounds. A metal-free catalytic reaction as an important green synthetic method has attracted much attention. A method for preparing quinoline from N-benzyl aniline by using radical cation salt as a catalyst was reported in 2015, but the development of the method was limited due to difficulty in synthesis of the catalyst [Liu J., Liu F., Zhu Y., Ma X., Jia X., Org. Lett., 2015, 17, 1409].

SUMMARY

The current invention provides a novel preparation method for quinoline compounds. Metal and solvent-free, mild and environmentally friendly reaction conditions, experimental simplicity and high yield are the useful features of current catalytic method.

The current invention adopts the following technical solution:

A green preparation method for quinoline compounds is provided. N-Substituted arylamine derivatives using as raw materials react with an arylacetylene or arylethylene derivatives for 24 hours at 80° C.–160° C. in the presence of Brönsted acid catalyst and oxidant without solvent, to obtain quinoline compounds. A synthetic route as follows:

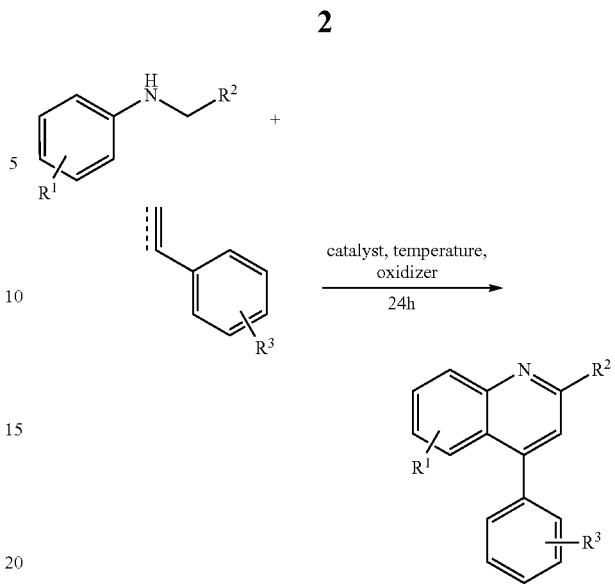

$R^1$ = H, alkyl and halogens;
$R^2$ = H, alkyl, ester, substituted phenyl and thiophenyl;
$R^3$ = H, alkyl, ester, halides, OMe and carbomethoxy;

$R^1$ is selected from H, alkyl and halogens;
$R^2$ is selected from H, alkyl, ester, substituted phenyl and thiophenyl;
$R^3$ is selected from H, alkyl, ester, halides, OMe and carbomethoxy;
a molar ratio of the N-Substituted arylamine derivative to the catalyst is 1:0.05 to 1:0.2; and
a molar ratio of the N-Substituted arylamine derivative to the arylacetylene or arylethylene derivative is 1:1 to 1:20.

The catalyst comprises acetic acid, trifluoroacetic acid, toluene-p-sulfonic acid and trifluoromethanesulfonic acid.

The oxidant comprises air, pure oxygen and peroxide.

Separation methods comprise recrystallization and column chromatography.

The recrystallization method uses solvents including benzene, alcohol, petroleum ether, acetonitrile, tetrahydrofuran, chloroform, hexane, acetone, ethyl acetate and dichloromethane.

When the column chromatography method is used to separate products, silica gel or alumina can be used as a stationary phase and an eluent is generally a mixture of polar and nonpolar solvents such as ethyl acetate-petroleum ether, ethyl acetate-hexane, dichloromethane-petroleum ether and methanol-petroleum ether.

The current invention has the some beneficial characteristics such as convenient operation, mild reaction conditions, environmentally friendly property and possibility of realizing industrialization, and provides the quinoline compounds in high yields. The quinoline compounds synthesized by this method can be further functionalized into various compounds which have potential applications in development and research of natural products, functional materials and fine chemicals.

DETAILED DESCRIPTION

Figure 1:
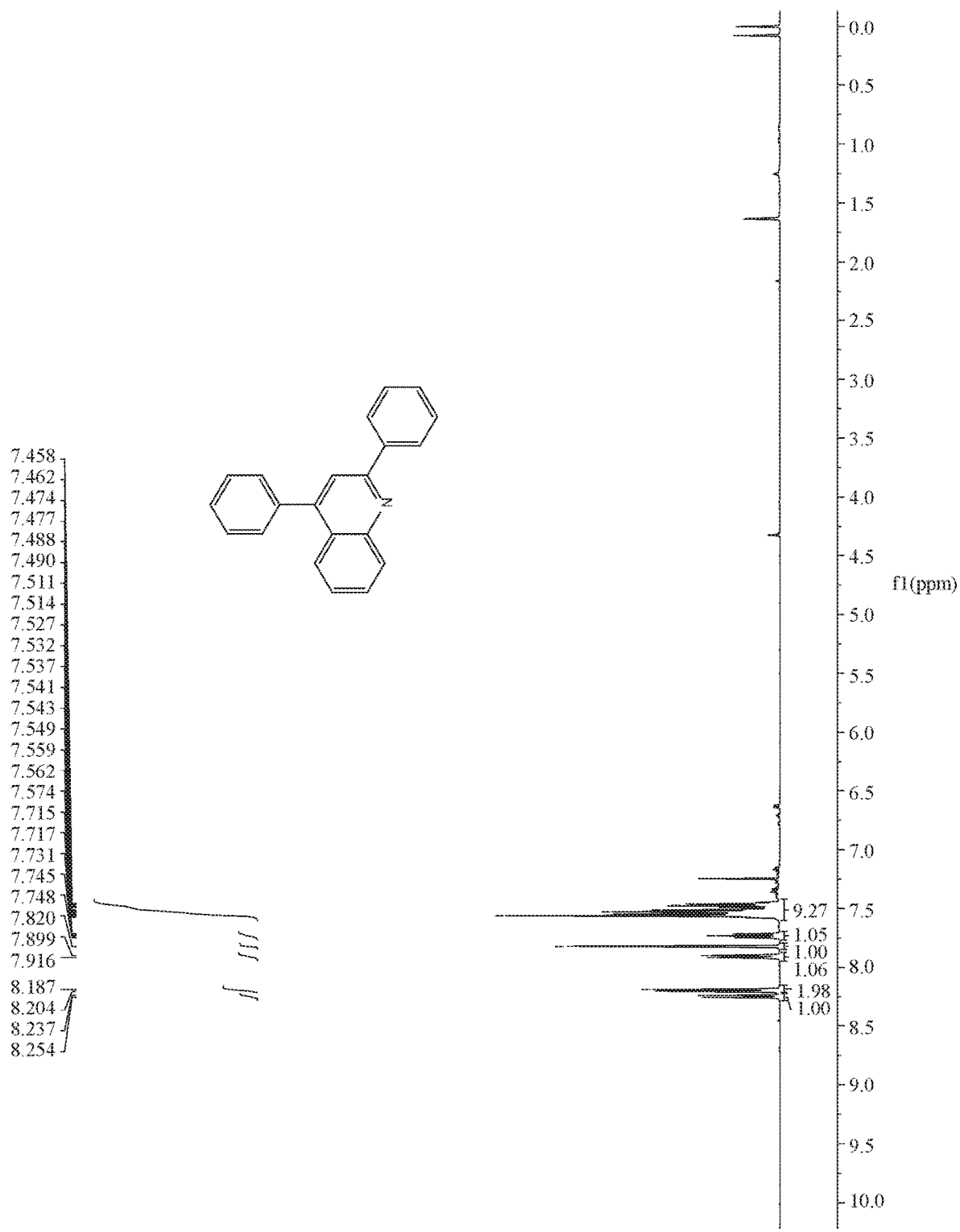
FIG. 1 is a $^1$H NMR of 2,4-diphenylquinoline in example 1.
Figure 2:
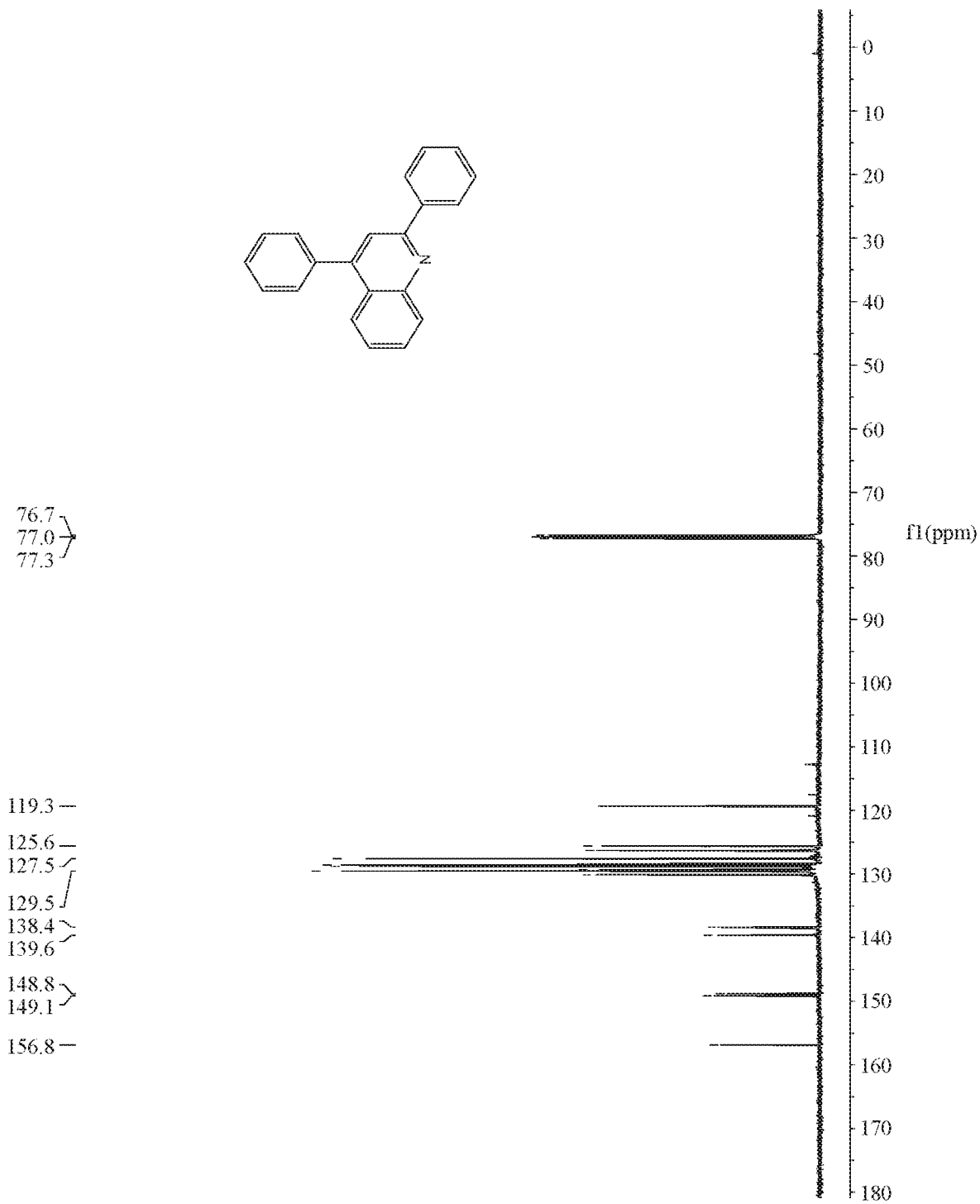
FIG. 2 is a $^{13}$C NMR of 2,4-diphenylquinoline in example 1.
Figure 3:
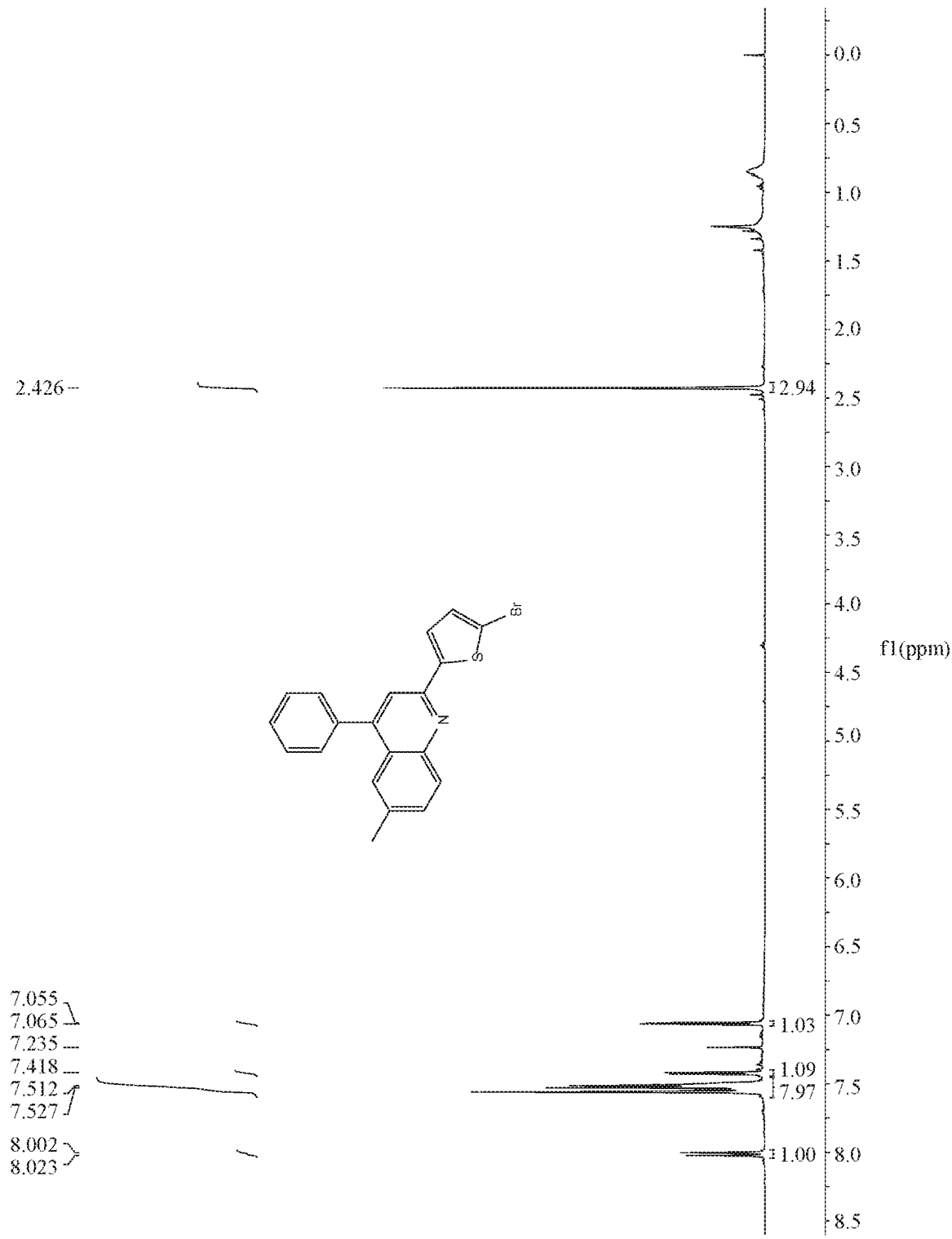
FIG. 3 is a $^1$H NMR of 2-(5-bromothiophen-2-yl)-6-methyl-4-phenylquinoline in example 2.
Figure 4:
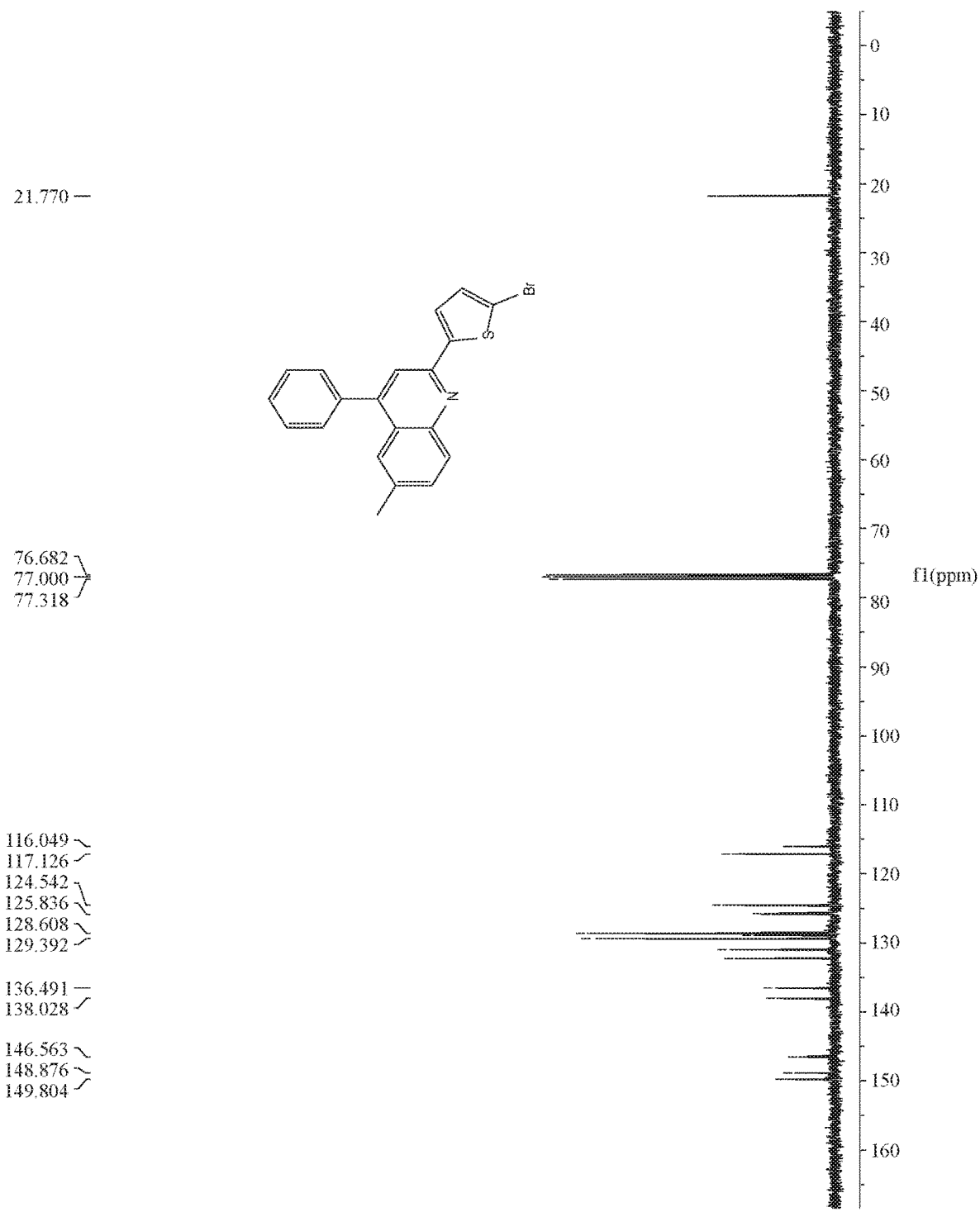
FIG. 4 is a $^{13}$C NMR of 2-(5-bromothiophen-2-yl)-6-methyl-4-phenylquinoline in example 2.
Figure 5:
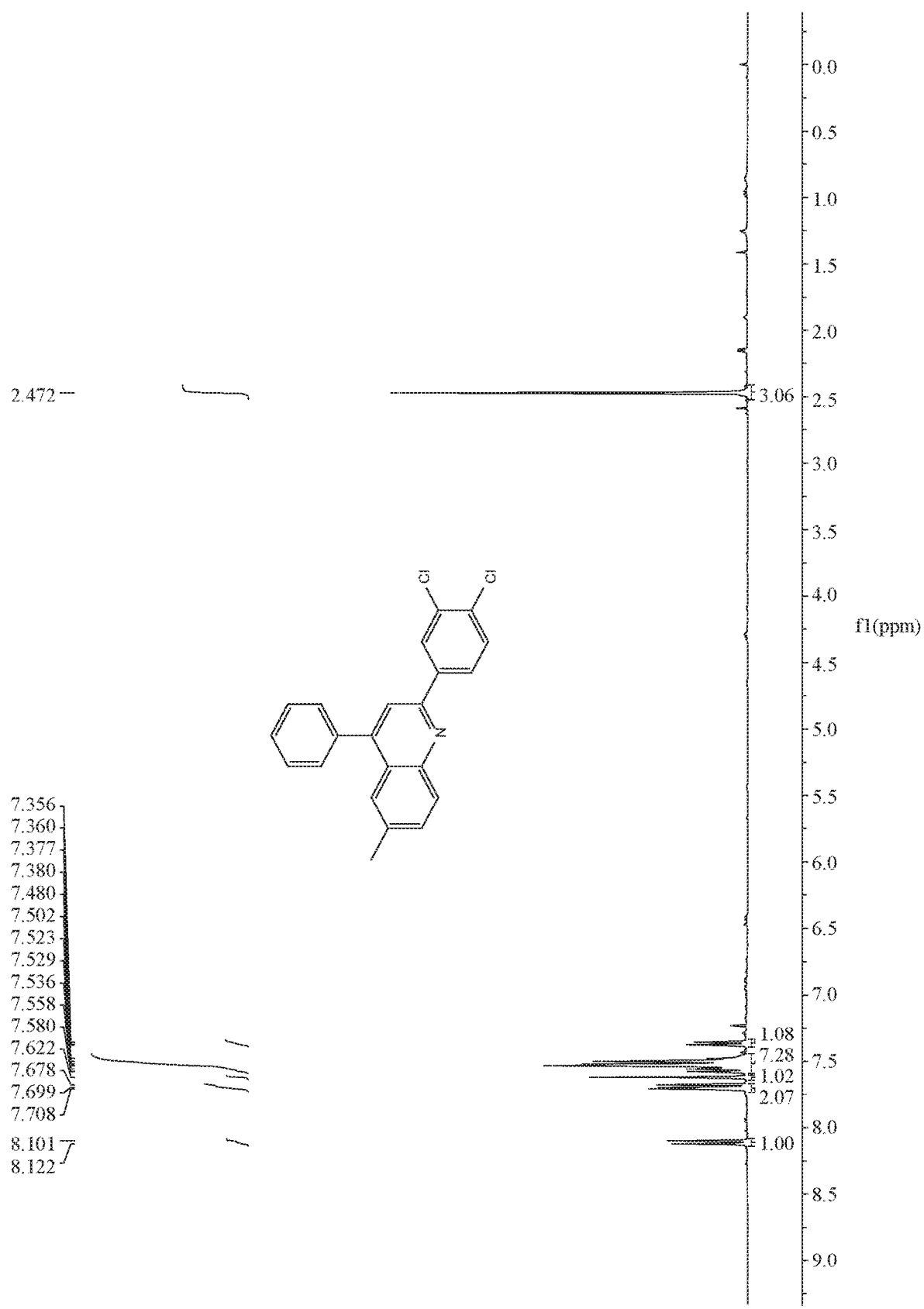
FIG. 5 is a $^1$H NMR of 2-(3, 4-dichlorophenyl)-6-methyl-4-phenylquinoline in example 3.
Figure 6:
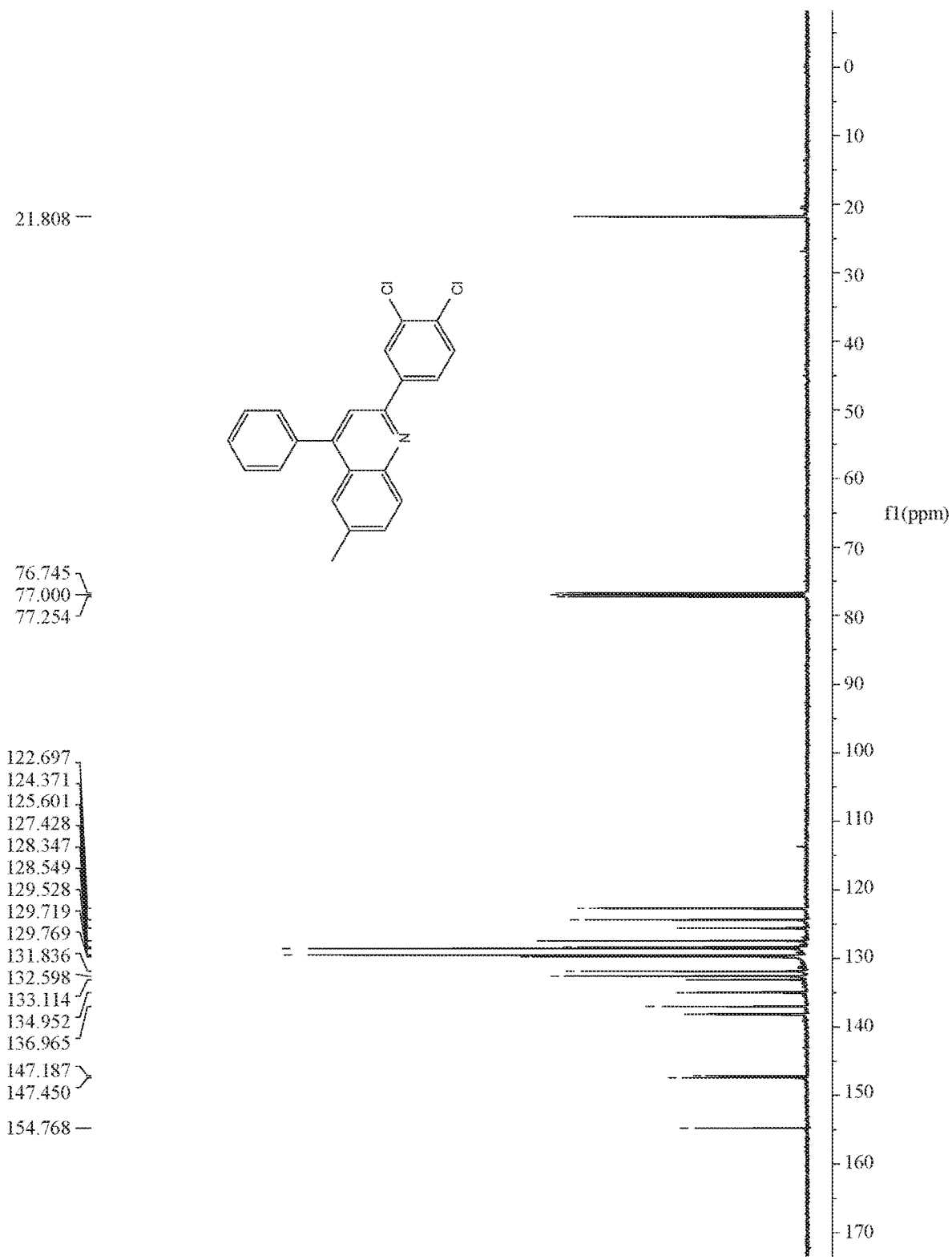
FIG. 6 is a $^{13}$C NMR of 2-(3, 4-dichlorophenyl)-6-methyl-4-phenylquinoline in example 3.
Figure 7:
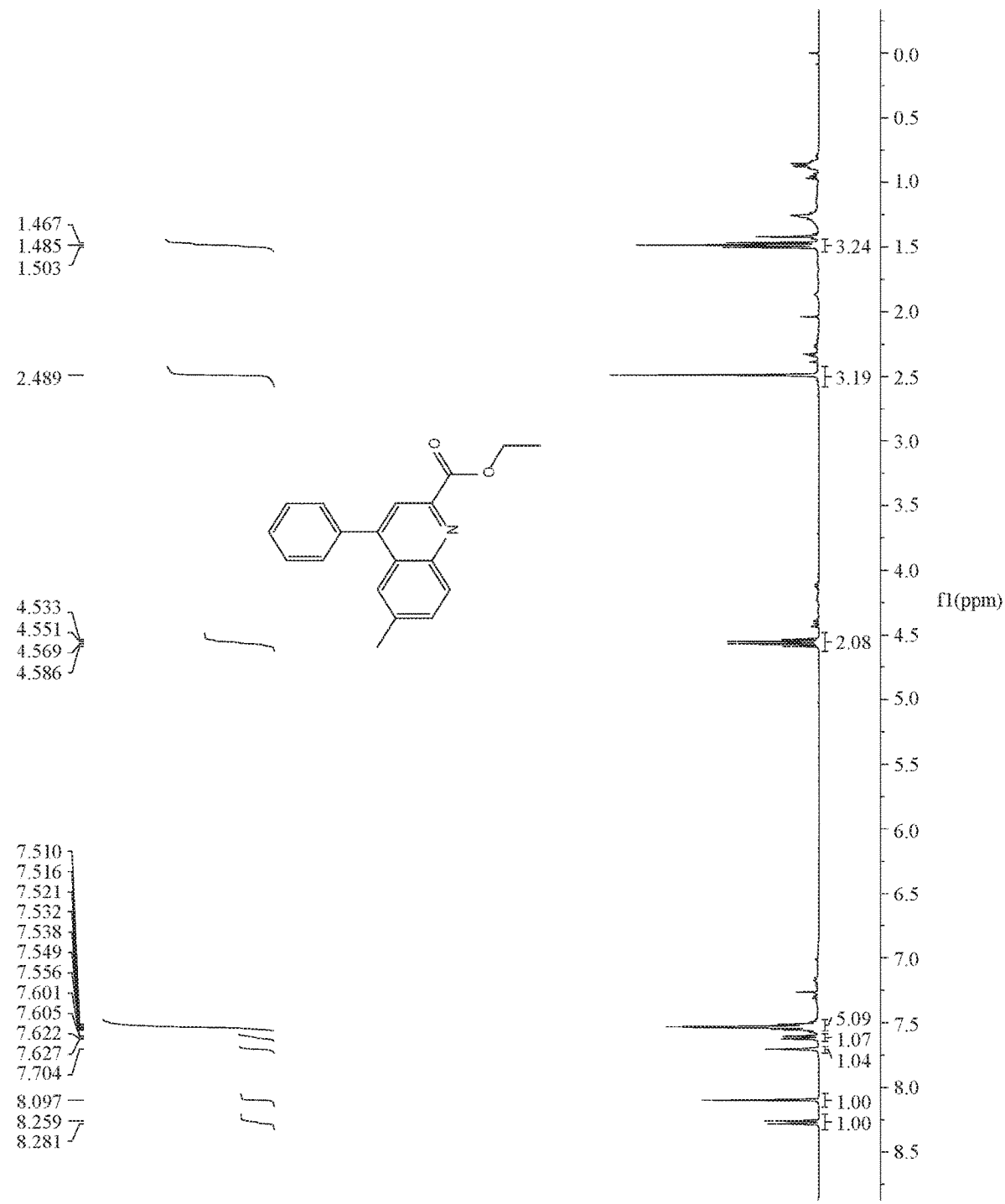
FIG. 7 is a $^1$H NMR of ethyl 2-(6-methyl-4-phenylquinolin-2-yl)acetate in example 4.
Figure 8:
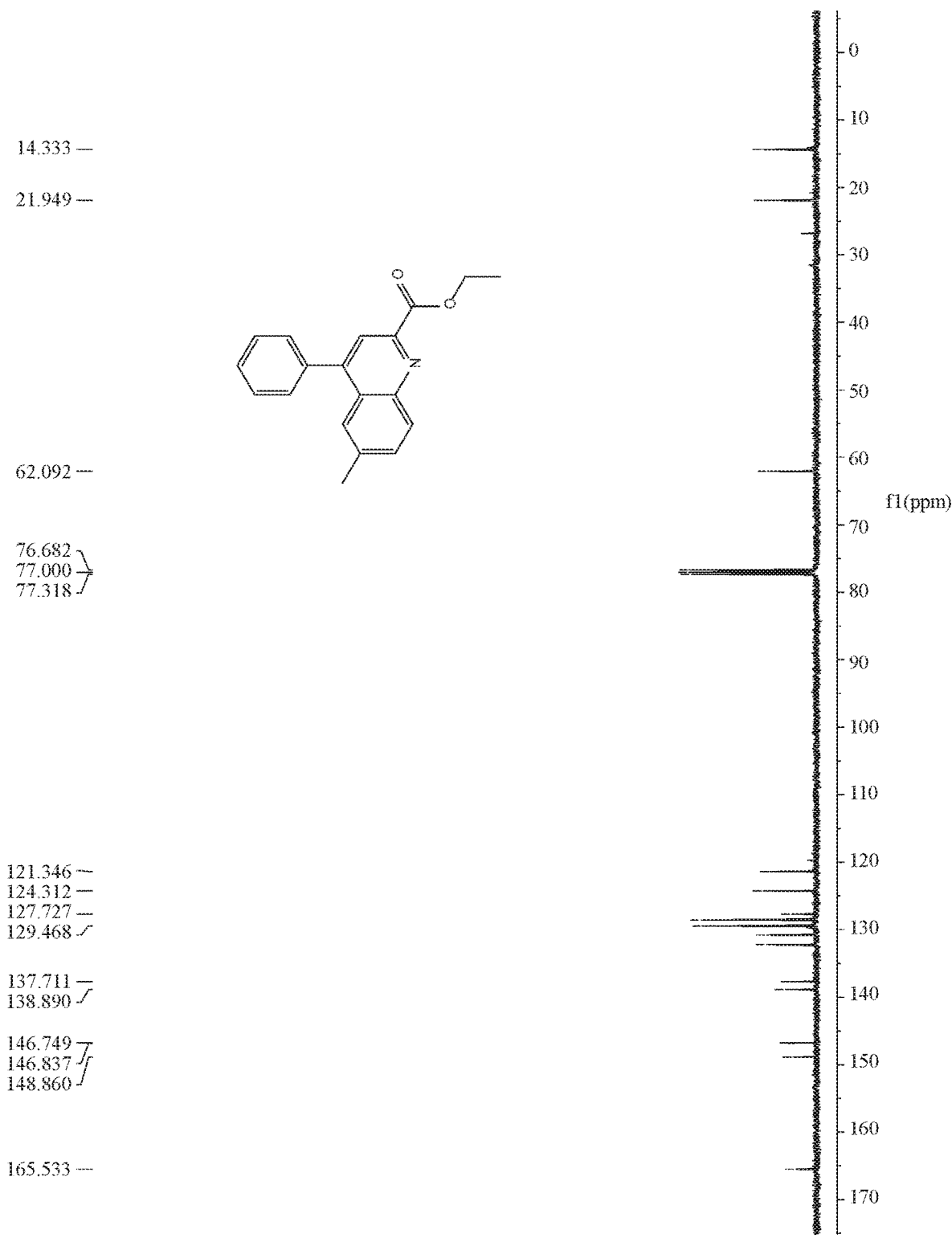
FIG. 8 is a $^{13}$C NMR of ethyl 2-(6-methyl-4-phenylquinolin-2-yl)acetate in example 4.
Figure 9:
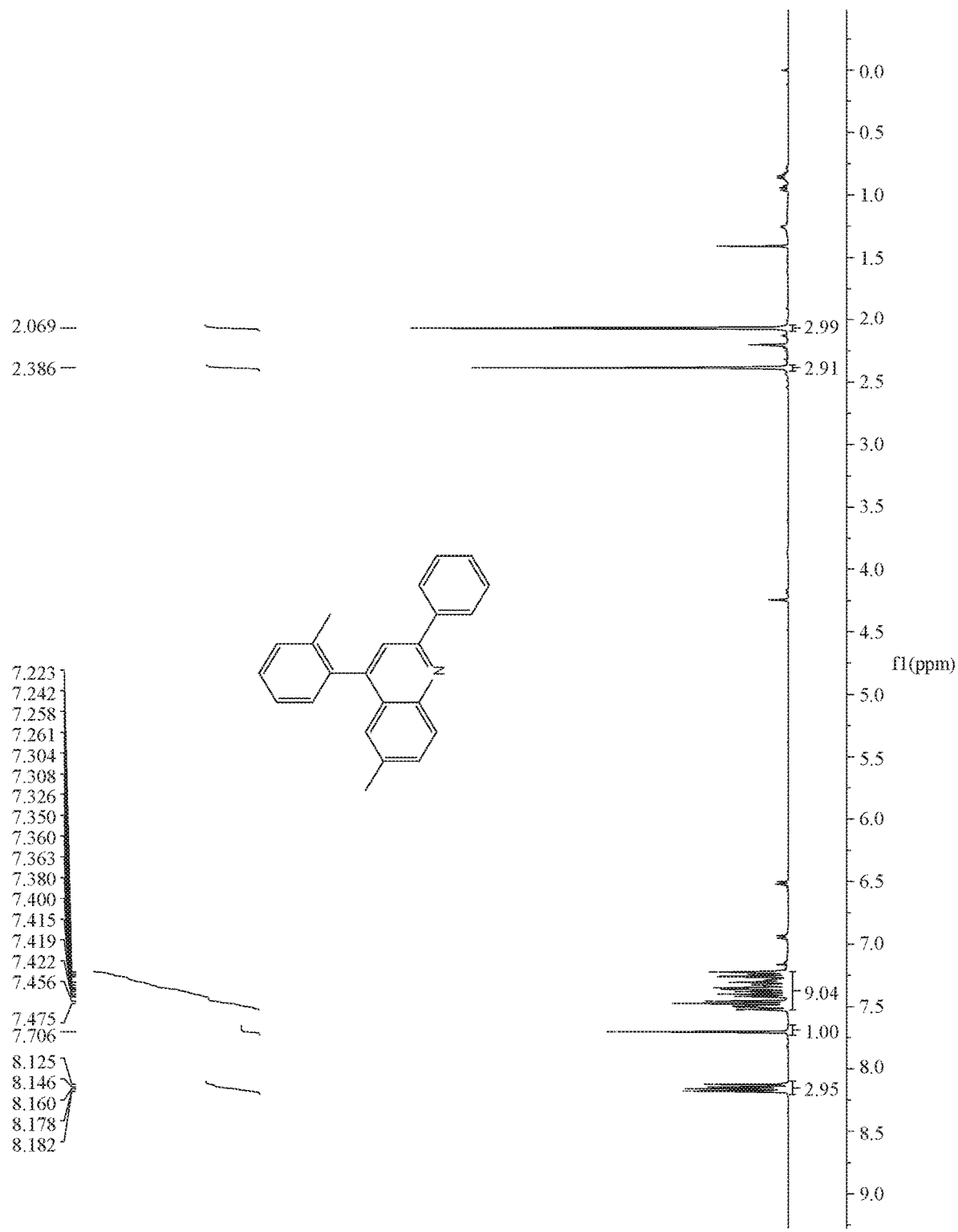
FIG. 9 is a $^1$H NMR of 6-methyl-2-phenyl-4-(o-tolyl)quinoline in example 5.
Figure 10:
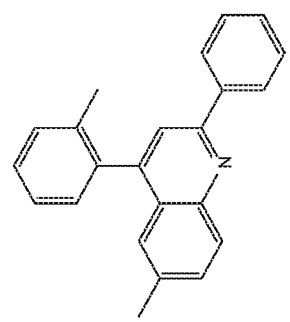
FIG. 10 is a $^{13}$C NMR of 6-methyl-2-phenyl-4-(o-tolyl)quinoline in example 5.
Figure 10:
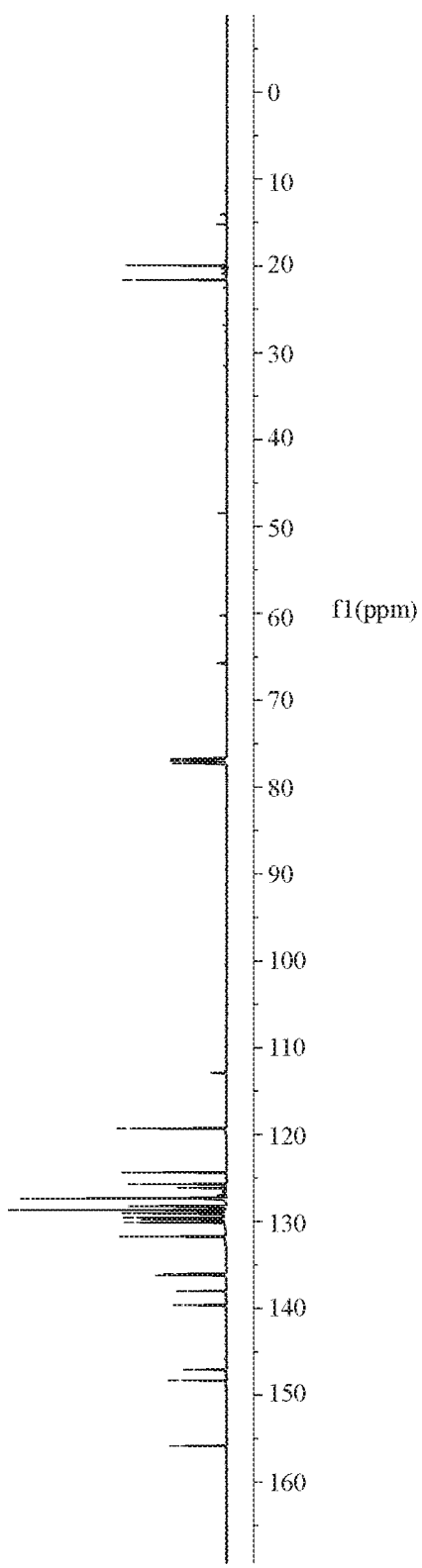
Figure 11:
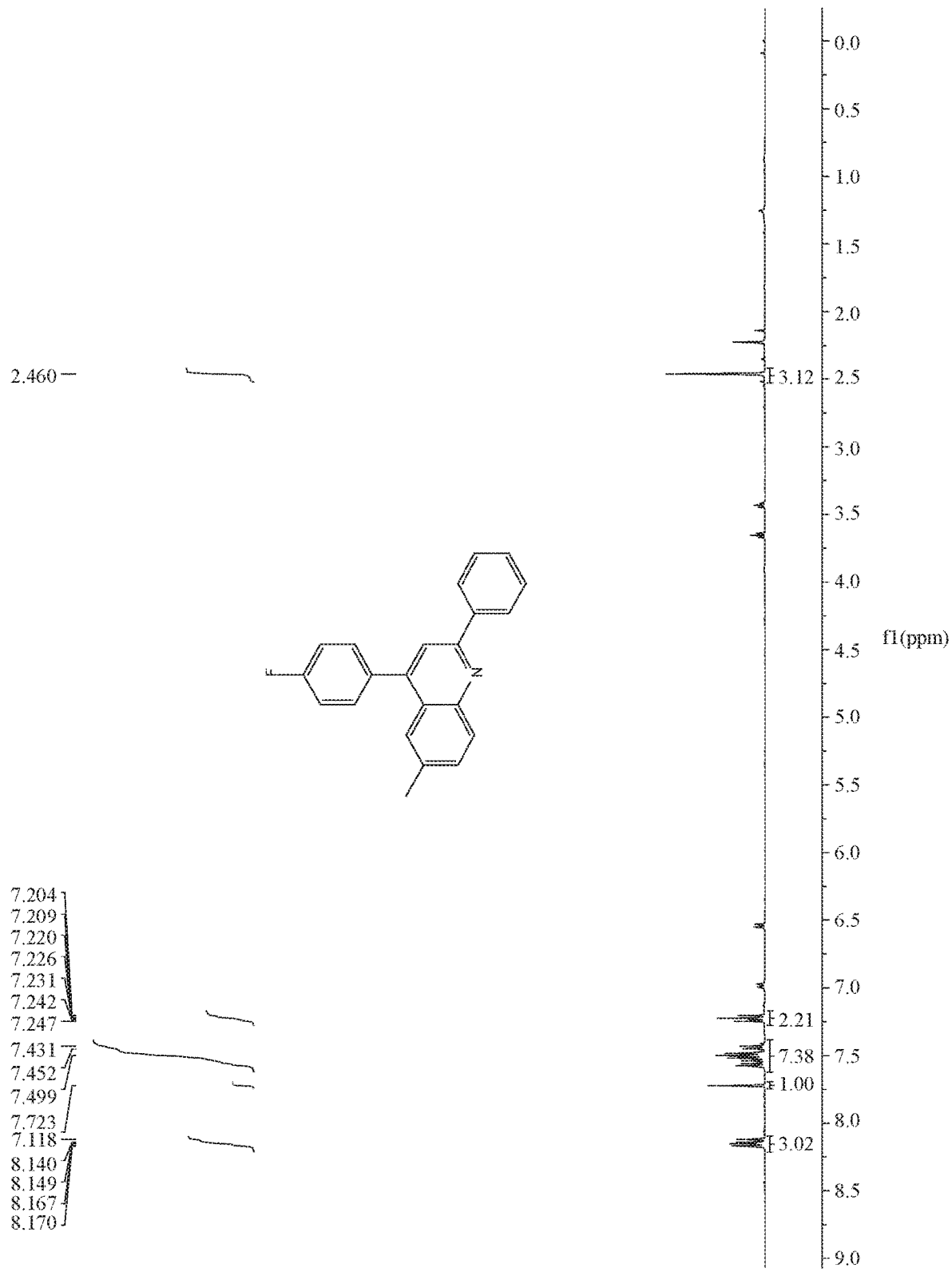
FIG. 11 is a $^1$H NMR of 4-(4-fluorophenyl)-6-methyl-2-phenylquinoline in example 6.
Figure 12:
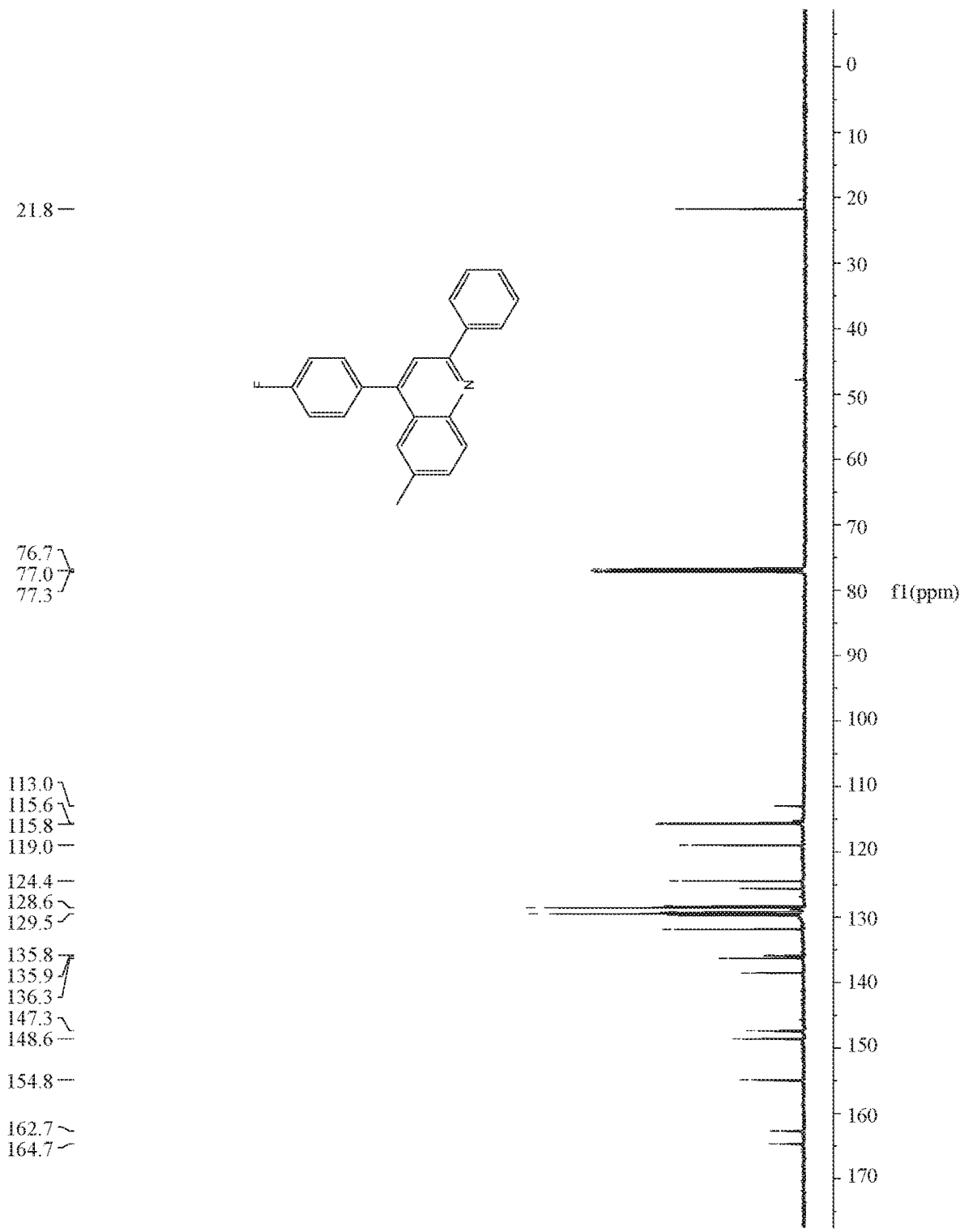
FIG. 12 is a $^{13}$C NMR of 4-(4-fluorophenyl)-6-methyl-2-phenylquinoline in example 6.
Figure 13:
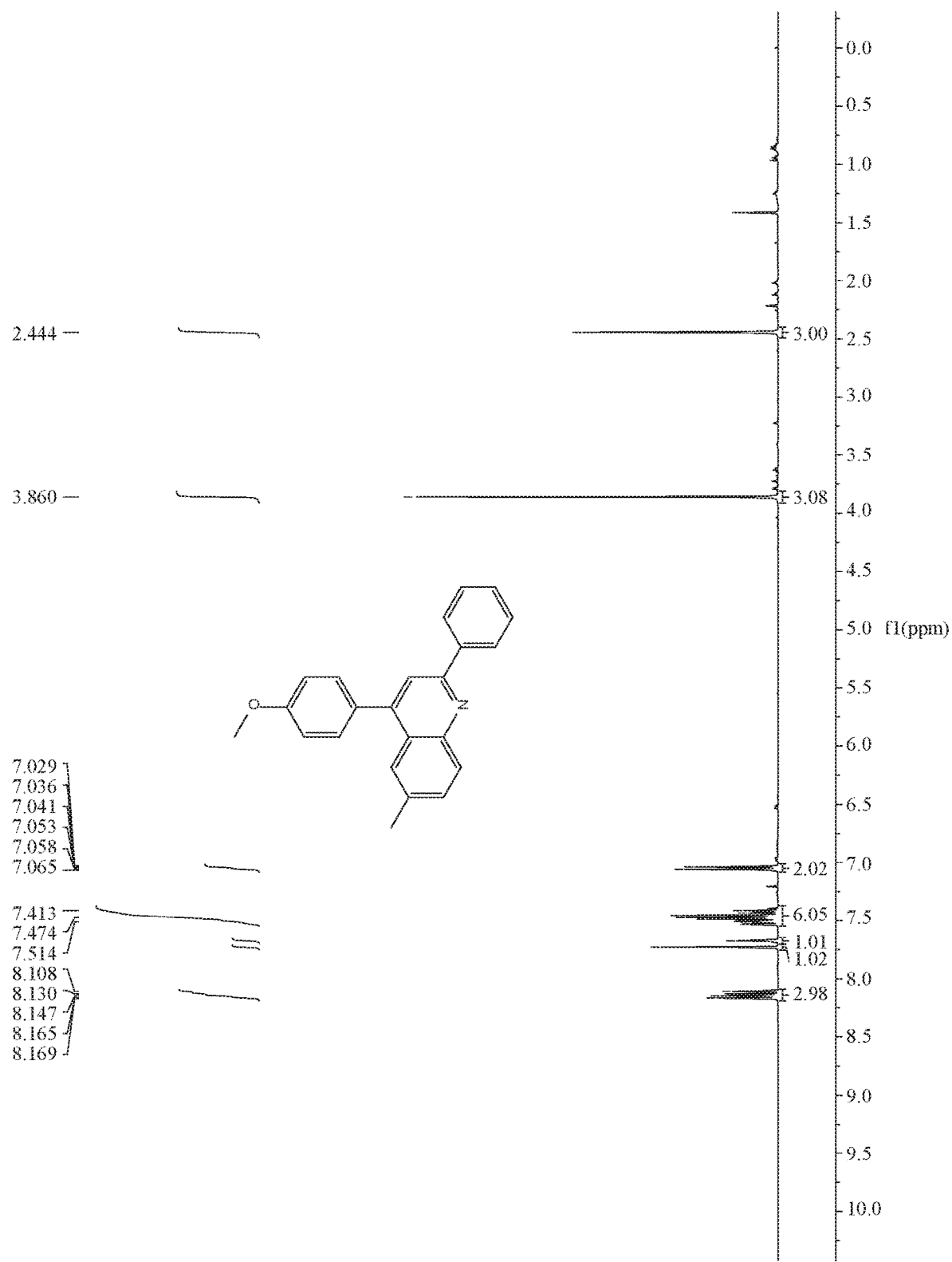
FIG. 13 is a $^1$H NMR of 4-(4-methoxyphenyl)-6-methyl-2-phenylquinoline in example 7.
Figure 14:
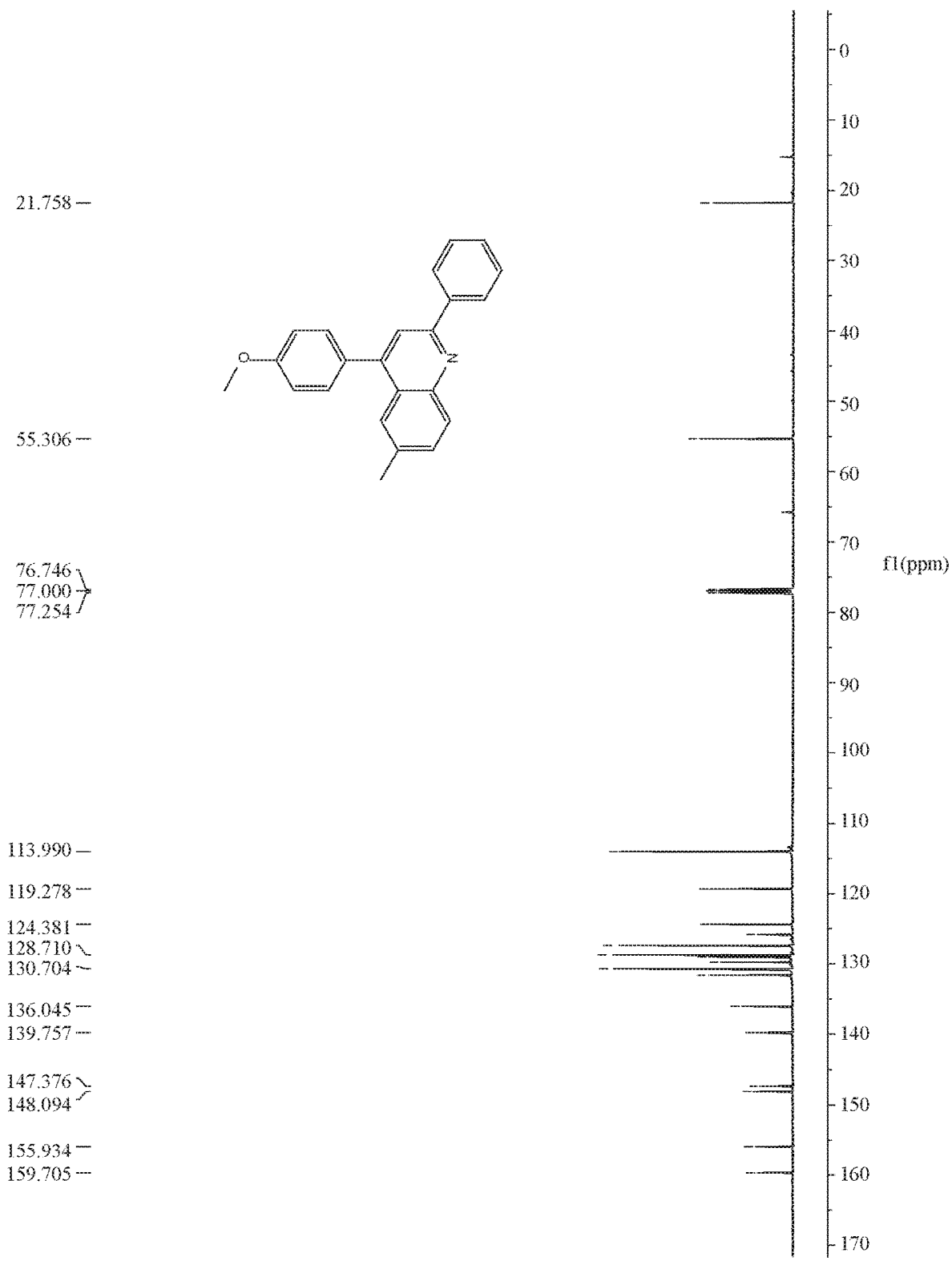
FIG. 14 is a $^{13}$C NMR of 4-(4-methoxyphenyl)-6-methyl-2-phenylquinoline in example 7.
Figure 15:
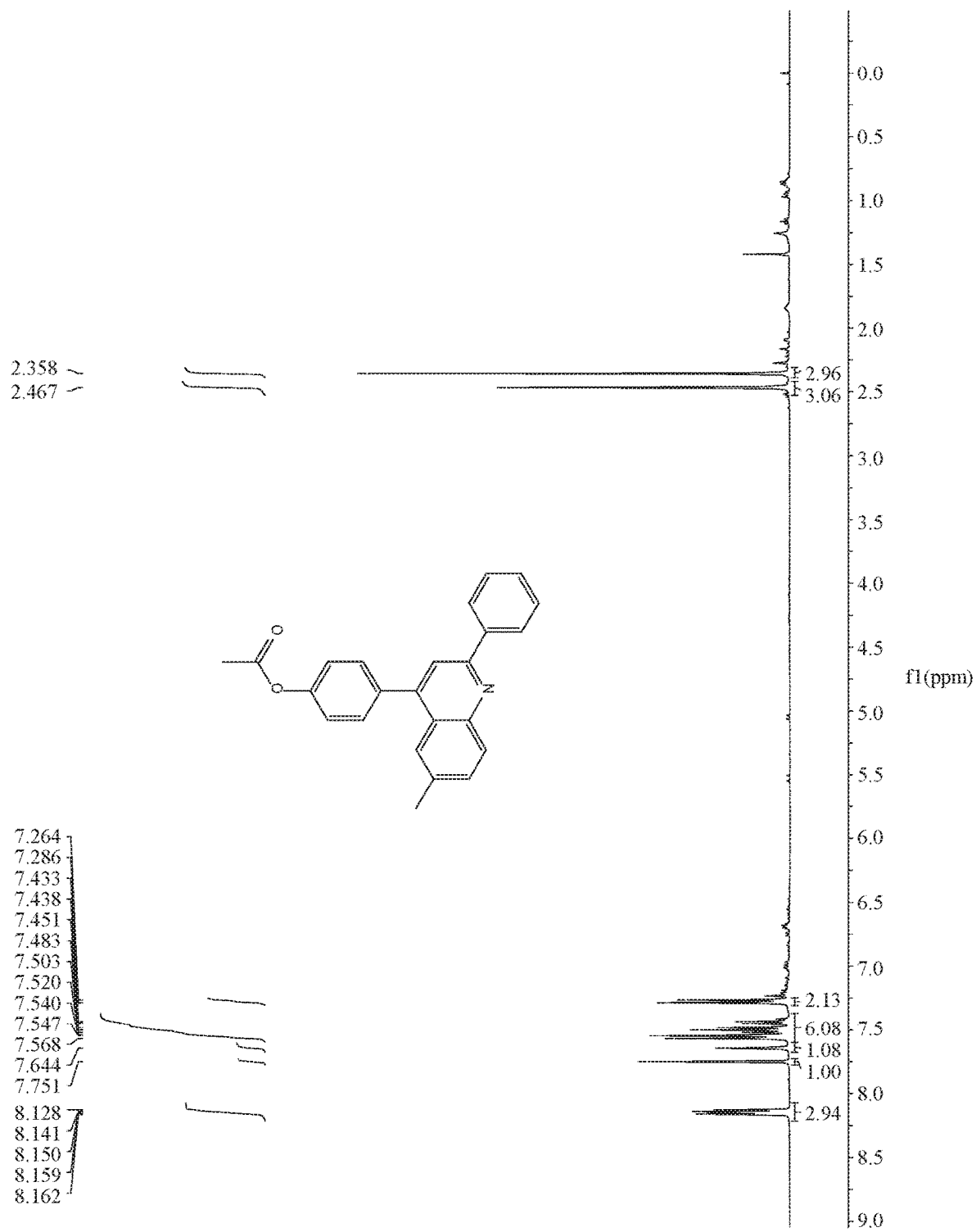
FIG. 15 is a $^1$H NMR of 4-(6-methyl-2-phenylquinolin-4-yl)phenyl acetate in example 8.
Figure 16:
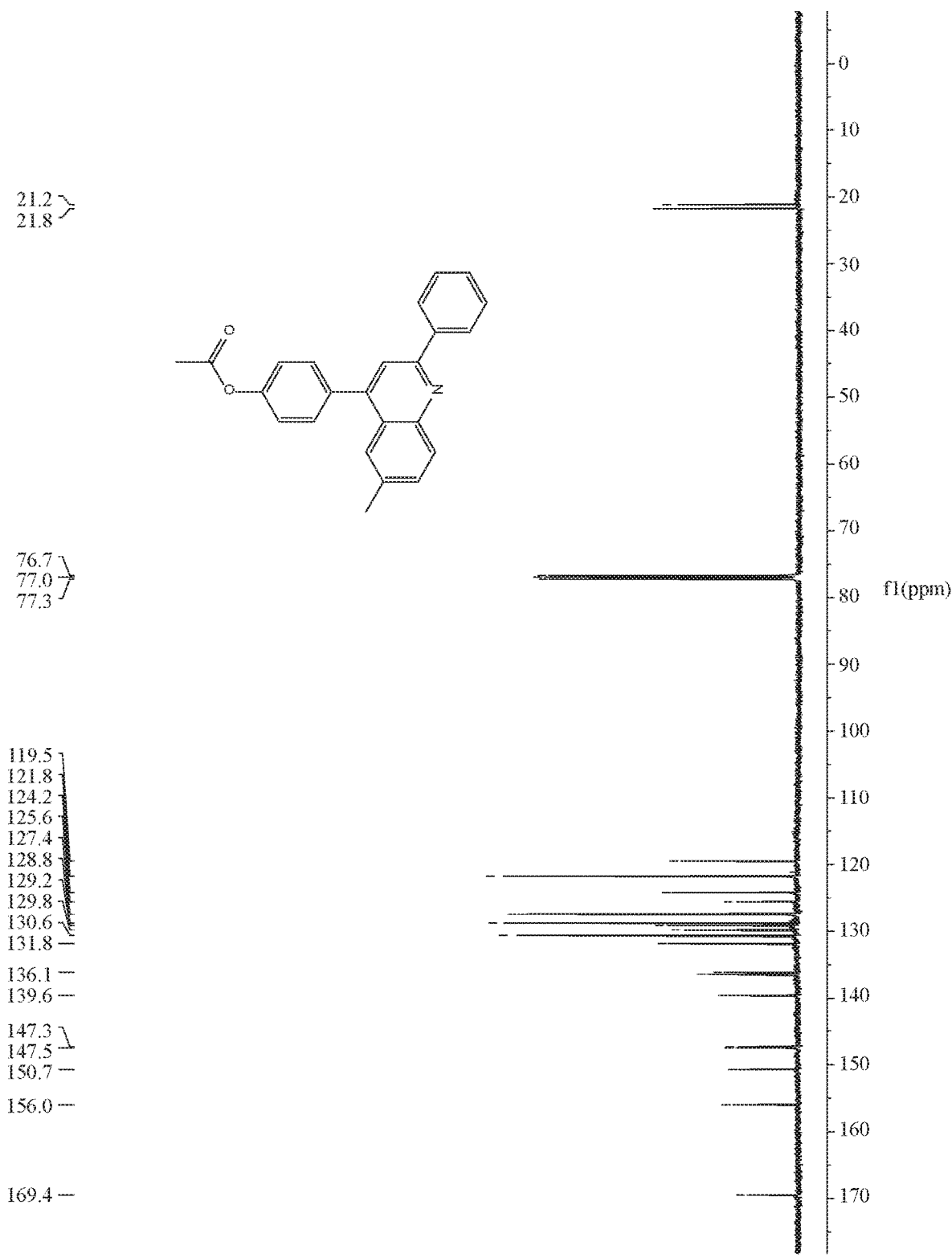
FIG. 16 is a $^{13}$C NMR of 4-(6-methyl-2-phenylquinolin-4-yl)phenyl acetate in example 8.

The preparation method for the quinoline compounds in current invention has the advantages of low cost of raw material, fewer reaction steps, mild reaction conditions, environmentally friendly property, convenient operation and high reaction yield.

The current invention is further described below in combination with the specific examples. The examples are only used for illustrating the current invention, not used for limiting the scope of current invention. Simple replacement or improvement made to the current invention by those skilled in the art belongs to the technical solution protected by the current invention.

Example 1: Synthesis of 2,4-diphenylquinoline

In a 25 mL reactor N-benzyl aniline (0.037 g, 0.2 mmol) and arylacetylene (0.102 g, 1.0 mmol) are added; trifluoroacetic acid (0.003 g, 0.03 mmol) is then added while stirred. The reaction mixtures materials are stirred for 24 h under an oxygen atmosphere at 80° C. Column chromatography separation (silica gel with 200-300 meshes; eluent, petroleum ether/dichloromethane=4/1) is conducted to obtain 0.047 g of 2,4-diphenylquinoline with a yield of 83%.

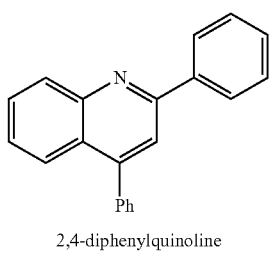 [SMILES: c1ccc(-c2cc(-c3ccccc3)c3ccccc3n2)cc1]

2,4-diphenylquinoline

Pale yellow oil; $^1$H NMR (400 MHz, CDCl$_3$): δ 8.23 (d, J=8.4 Hz, 1H), 8.19 (d, J=8.4 Hz, 2H), 7.91 (d, J=8.3 Hz, 1H), 7.82 (s, 1H), 7.75-7.71 (m, 1H), 7.57-7.46 (m, 9H); $^{13}$C NMR (125 MHz, CDCl$_3$): δ 156.8, 149.1, 148.8, 139.6, 138.4, 130.1, 129.5, 129.5, 129.3, 128.8, 128.6, 128.4, 127.5, 126.3, 125.7, 125.6, 119.3.

Example 2: synthesis of 2-(5-bromothiophen-2-yl)-6-methyl-4-phenylquinoline

Operation is the same as that in example 1. N((5-bromothiophen-2-yl)methyl)-4-methylaniline reacts with arylacetylene to produce 0.059 g of 2-(5-bromothiophen-2-yl)-6-methyl-4-phenylquinoline with a Yield of 78%.

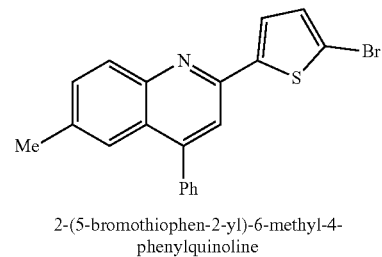 [SMILES: Cc1ccc2nc(-c3ccc(Br)s3)cc(-c3ccccc3)c2c1]

2-(5-bromothiophen-2-yl)-6-methyl-4-phenylquinoline

Brown solid; melting point of 181.1-182.0° C.; $^1$H NMR (400 MHz, CDCl$_3$): δ8.01 (d, J=8.6 Hz, 1H), 7.56-7.50 (m, 8H), 7.42 (d, J=4.0 Hz, 1H), 7.06 (d, J=4.0 Hz, 1H), 2.43 (s, 3H); $^{13}$C NMR (100 MHz, CDCl$_3$): δ 149.8, 148.9, 146.6, 138.0, 136.5, 132.2, 131.0, 129.4, 128.9, 128.6, 128.5, 125.8, 125.7, 124.5, 117.1, 116.0, 21.8; HRMS (ESI, m/z) calcd for C$_{20}$H$_{15}$NBrS$^+$: 380.0103 [M+H]$^+$; found: 380.0109; IR (neat) 3046, 2959, 2825, 1608, 1563, 1442, 1021, 850, 790, 732, 574 cm$^{-1}$.

Example 3: Synthesis of 2-(3, 4-dichlorophenyl)-6-methyl-4-phenylquinoline

Operation is the same as that in example 1. N-(3,4-dichlorobenzyl)-4-methylaniline reacts with arylacetylene to produce 0.067 g of 2-(3, 4-dichlorophenyl)-6-methyl-4-phenylquinoline with a yield of 92%.

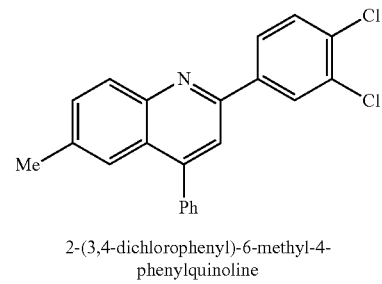

2-(3,4-dichlorophenyl)-6-methyl-4-phenylquinoline

White solid; melting point of 143.0-143.6° C.; $^1$H NMR (400 MHz, CDCl$_3$): δ 8.11 (d, J=8.5 Hz, 1H), 7.71-7.68 (m, 2H), 7.62 (s, 1H), 7.58-7.48 (m, 7H), 7.37 (dd, J=8.5, 2.1 Hz, 1H), 2.47 (s, 3H); $^{13}$C NMR (125 MHz, CDCl$_3$): δ 154.8, 147.5, 147.2, 138.1, 138.1, 137.0, 135.0, 133.1, 132.6, 131.8, 129.8, 129.7, 129.5, 128.5, 128.3, 127.4, 125.6, 124.4, 122.7, 21.8.

Example 4: Synthesis of ethyl 2-(6-methyl-4-phenylquinolin-2-yl)acetate

Operation is the same as that in example 1. Ethyl p-tolylglycinate reacts with arylacetylene to produce 0.051 g of ethyl 2-(6-methyl-4-phenylquinolin-2-yl)acetate with a yield of 87%.

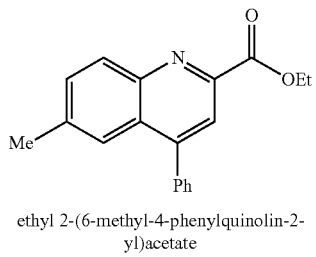 [SMILES: CCOC(=O)c1cc(-c2ccccc2)c2cc(C)ccc2n1]

ethyl 2-(6-methyl-4-phenylquinolin-2-yl)acetate

Brown solid; melting point of 115.4-116.1° C.; $^1$H NMR (400 MHz, CDCl$_3$): 58.27 (d, J=8.7 Hz, 1H), 8.10 (s, 1H), 7.70 (s, 1H), 7.61 (dd, J=8.7, 1.8 Hz, 1H), 7.56-7.51 (m, 5H), 4.56 (q, J=7.1 Hz, 2H), 2.49 (s, 3H), 1.49 (t, J=7.1 Hz, 3H); $^{13}$C NMR (100 MHz, CDCl$_3$): δ 165.5, 148.9, 146.8, 146.7, 138.9, 137.7, 132.3, 130.8, 129.5, 128.6, 128.5, 127.7, 124.3, 121.3, 62.1, 21.9, 14.3.

Example 5: Synthesis of 6-methyl-2-phenyl-4-(o-tolyl)quinoline

In a 25 mL reactor N-benzyl-4-methylaniline (0.039 g, 0.2 mmol) and 1-methyl-2-vinylbenzene (0.236 g, 2.0 mmol) are added; toluene-p-sulfonic acid (0.003 g, 0.02 mmol) is then added while stirred. The reaction mixtures are stirred for 24 h under air at 130° C. Column chromatography separation (silica gel with 200-300 meshes; eluent, petroleum ether/dichloromethane=2:1) is conducted to obtain 0.048 g of 6-methyl-2-phenyl-4-(o-tolyl)quinoline with a yield of 78%.

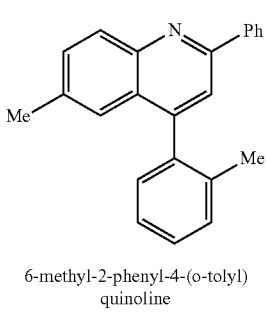 [SMILES: Cc1ccc2nc(-c3ccccc3)cc(-c3ccccc3C)c2c1]

6-methyl-2-phenyl-4-(o-tolyl)quinoline

Brown solid; melting point of 122.1-123.0° C.; $^1$H NMR (400 MHz, CDCl$_3$): δ 8.18-8.12 (m, 3H), 7.71 (s, 1H), 7.53-7.22 (m, 9H), 2.39 (s, 3H), 2.07 (s, 3H); $^{13}$C NMR (125 MHz, CDCl$_3$): δ 155.9, 148.3, 147.1, 139.6, 138.0, 136.2, 136.0, 131.7, 130.1, 129.7, 129.6, 129.1, 128.7, 128.2, 127.4, 126.1, 125.7, 124.4, 119.3, 21.6, 20.0.

Example 6: 4-(4-fluorophenyl)-6-methyl-2-phenylquinoline

Operation is the same as that in example 5. N-benzyl-4-methylaniline reacts with 1-fluoro-4-vinylbenzene to produce 0.044 g of 4-(4-Fluorophenyl)-6-methyl-2-phenylquinoline with a yield of 71%.

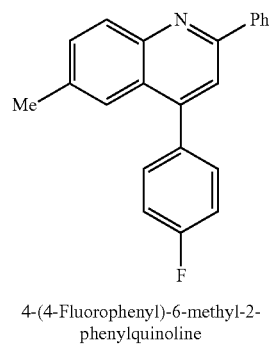 [SMILES: Cc1ccc2nc(-c3ccccc3)cc(-c3ccc(F)cc3)c2c1]

4-(4-Fluorophenyl)-6-methyl-2-phenylquinoline

Yellow solid; melting point of 112.9-113.5° C.; $^1$H NMR (400 MHz, CDCl$_3$): δ 8.17-8.12 (m, 3H), 7.72 (s, 1H), 7.58-7.43 (m, 7H), 7.25-7.20 (m, 2H), 2.46 (s, 3H); $^{13}$C NMR (125 MHz, CDCl$_3$): δ 163.7 (d, $^1J_{C-F}$=248.0), 154.8, 148.6, 147.3, 138.5, 136.3, 135.9 (d, $^4J_{C-F}$=3.0 Hz), 131.8, 129.7, 129.5, 129.2 (d, $^3J_{C-F}$=8.4 Hz), 128.6, 128.3, 125.6, 124.4, 119.0, 115.7 (d, $^2J_{C-F}$=21.5 Hz), 113.0, 21.8.

Example 7: Synthesis of 4-(4-methoxyphenyl)-6-methyl-2-phenylquinoline

In a 25 mL reactor N-benzyl-4-methylaniline (0.039 g, 0.2 mmol) and 1-ethynyl-4-methoxybenzene (0.198 g, 1.5 mmol) are added; trifluoromethanesulfonic acid (0.005 g, 0.03 mmol) is then added while stirred. The reaction mixtures are stirred for 24 h under an oxygen atmosphere at 110° C. Column chromatography separation (silica gel with 200-300 meshes; eluent, petroleum ether/ethyl acetate=5:1) is conducted to obtain 0.056 g of 4-(4-methoxyphenyl)-6-methyl-2-phenylquinoline with a yield of 86%.

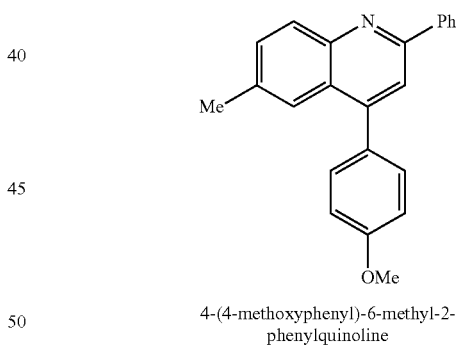

4-(4-methoxyphenyl)-6-methyl-2-phenylquinoline

Yellow solid; melting point of 104.7-105.8° C.; $^1$H NMR (400 MHz, CDCl$_3$): δ 8.17-8.11 (m, 3H), 7.73 (s, 1H), 7.67 (s, 1H), 7.54-7.41 (m, 6H), 7.07-7.03 (m, 2H), 3.86 (s, 3H), 2.44 (s, 3H); $^{13}$C NMR (125 MHz, CDCl$_3$): δ 159.7, 155.9, 148.1, 147.4, 139.8, 136.0, 131.6, 130.8, 130.7, 129.8, 129.0, 128.7, 127.4, 125.8, 124.4, 119.3, 114.0, 55.3, 21.8.

Example 8: Synthesis of 4-(6-methyl-2-phenylquinolin-4-yl)phenyl acetate

Operation is the same as that in example 7. N-benzyl-4-methylaniline reacts with 4-ethynylphenyl acetate to produce 0.048 g of 4-(6-methyl-2-phenylquinolin-4-yl)phenyl acetate with a yield of 68%.

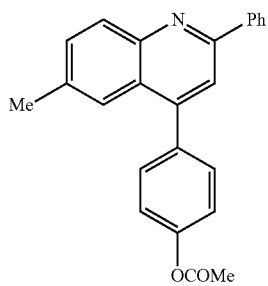

4-(6-methyl-2-phenylquinolin-4-yl) phenyl acetate

Brown solid; melting point of 126.5-127.3° C.; $^1$H NMR (400 MHz, CDCl$_3$): δ 8.16-8.13 (m, 3H), 7.75 (s, 1H), 7.64 (s, 1H), 7.57-7.43 (m, 6H), 7.27 (d, J=8.5 Hz, 2H), 2.47 (s, 3H), 2.36 (s, 3H); $^{13}$C NMR (125 MHz, CDCl$_3$): δ 169.4, 156.0, 150.7, 147.5, 147.3, 139.6, 136.4, 136.1, 131.8, 130.6, 129.8, 129.2, 128.8, 127.4, 125.6, 124.2, 121.8, 119.5, 21.8, 21.2.

We claim:

1. A green preparation method for quinoline compounds, wherein N-Substituted arylamine derivatives as raw material reacting with arylacetylene or arylethylene derivative for 24 hours at 80° C.–160° C. in the presence of Brönsted acid catalyst and oxidant without solvent, to obtain quinoline compounds, wherein a synthetic route as follows:

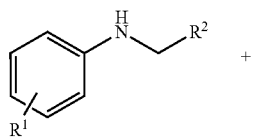
+

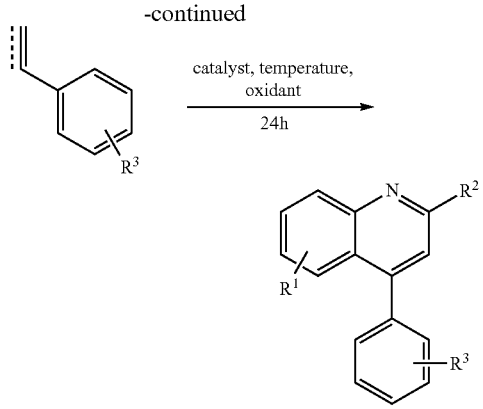

$R^1$ = H, alkyl and halogens;
$R^2$ = H, alkyl, ester, substituted phenyl and thiophenyl;
$R^3$ = H, alkyl, ester, halides, OMe and carbomethoxy;

$R^1$ is selected from H, alkyl and halogens;
$R^2$ is selected from H, alkyl, ester, substituted phenyl and thiophenyl;
$R^3$ is selected from H, alkyl, ester, halides, OMe and carbomethoxy;
a molar ratio of the N-Substituted arylamine derivative to the catalyst is 1:0.05 to 1:0.2; and
a molar ratio of the N-Substituted arylamine derivative to the arylacetylene or arylethylene derivative is 1:1 to 1:20.

2. The preparation method according to claim 1, wherein the catalyst is acetic acid, trifluoroacetic acid, toluene-p-sulfonic acid or trifluoromethanesulfonic acid.

3. The preparation method according to claim 1, wherein the oxidant is air, pure oxygen or peroxide.

* * * * *